US00PP07910P

United States Patent [19]

Veenstra

[11] Patent Number: Plant 7,910

[45] Date of Patent: Jul. 14, 1992

[54] ASIATIC LILY NAMED SUPER GAZER

[75] Inventor: Rien Veenstra, Wilsonville, Oreg.

[73] Assignee: Oregon Bulb Farms, Inc., Aurora, Oreg.

[21] Appl. No.: 504,286

[22] Filed: Mar. 19, 1990

[51] Int. Cl.[5] ..... A01H 5/00

[52] U.S. Cl. ..... Plt./87.4

[58] Field of Search ..... Plt./68

*Primary Examiner*—James R. Feyrer

[57] ABSTRACT

A new variety of asiatic lily having very large flowers particularly distinguished by the overall red purple coloring of its tepals which extend to the tepal margins the edges of which are white. This new variety is further distinguished by its profuse production, once annually in mid-season, of flowers which are carried on strong upright stems in a raceme cluster at a height of about 100 cm. above the base of the plant.

1 Drawing Sheet

BACKGROUND OF THE NEW PLANT

This new lily originated as a seedling hybrid resulting from the cross of an unnamed variety selected from plants of the crimson glory strain with pollen from the variety Star Gazer (U.S. Plant Pat. No. 4,085) at Sandy, Oreg. This seedling having been selected by me for propagation because of its profuse production of flowers carried adjacent the top of relatively tall upright stems as well as because of its strong red purple flower coloration. Propagation of this new plant was done under my direction at Sandy, Oreg. by tissue culture as well as by scales with such material success that propagation through several successive generations was done in the same manner at Sandy, Oreg. and this conclusively demonstrated that the distinctive characteristics of the selected seedling were carried on from generation to generation and appear to be firmly fixed. Propagation of this new lily variety for commercial purposes is now being done by Oregon Bulb Farms, Inc. at Aurora, Oreg.

DESCRIPTION OF THE DRAWING

This new variety of lily plant is illustrated by the accompanying full color photographic drawing which shows a face view of a fully open flower, the color rendition being as nearly true as can be reasonably obtained by conventional photographic procedures.

DESCRIPTION OF THE NEW PLANT

The following is a detailed description of my new oriental lily variety as observed from plants being grown at Aurora, Oreg., the color designations being according to the R.H.S. Colour Chart published by The Royal Horticultural Society of London, England.

THE PLANT

Origin: Seedling.

Parentage:

*Seed parent.*—An unnamed and unpatented clone selected from the crimson glory strain.

*Pollen parent.*—Star Gazer (U.S. Plant Pat. No. 4,085).

Classification:

*Botanic.*—Division — VIIC Oriental Hybrid.

*Commercial.*—Hybrid Lilium clone.

Form: Single upright stem from each bulb.

Height: About 105 cm.

Growth: Vigorous, upright and very strong.

Foliage:

*Quantity.*—Abundant.

*Size of leaf.*—About 18.5 cm. long and about 4.4 cm. wide.

*Shape of leaf.*—Ovate with entire margins.

*Texture.*—Leathery.

*Aspect.*—Glossy.

*Color.*—Upper side — very dark green. Under side — lighter green.

Ribs and veins: Distinct, longitudinal veins from base to tip.

Bulbs:

*Size.*—Up to about 25 cm. in circumference for commercial use.

*Color.*—White with pink overtones.

THE BUD

Shape: Long ovoid with an obtuse apex.

Size: About 11 to 13 cm. in length and about 3 cm. in diameter.

Rate of opening: The bud opens slowly in response to light.

Color of tepals:

*When sepals first divide.*—Red Purple 63-D.

*When tepals begin to unfurl.*—Red Purple 63-C.

Peduncle:

*Character.*—Erect.

*Color.*—Green 146-D.

THE FLOWER

Blooming habit: Annually and profusely at mid-season.

Size of flower: Very Large.

*Diameter.*—About 7 inches.

Borne: As a cluster with raceme arrangement on a tall, single stem.

Shape:

*When bloom first opens.*—Cup shaped.

*When bloom matures.*—A flatened cup.

Tepalage:

*Number.*—Six.

*Arrangement.*—Hexagonally and imbricated.

*Form.*—Ovate with entire, somewhat undulate margin with acute apex.

*Texture.*—Leathery.

*Aspect.*—Satiny.

*Color.*—Outer tepals — body, Red Purple 63-A with Greyed Purple 187-C on midrib. Shading laterally to Red Purple 63-C towards tepal edges. Base — Green Yellow 144-B. Reverse side — Red Purple 63-B. Inside tepals — body, Red Purple 63-A. Base — Green Yellow 144-B. Reverse side — Red Purple 63-B.

*Spotting.*—Greyed purple 187-B extending about two-thirds of the tepal length.

*Papillae.*—Distinct and found on each side of the nectaries extending about two-thirds of the nectary length.

Flower stem:

*Length.*—About 105 cm.

*Color.*—Yellow Green 146-D.

*Character.*—Very strong and upright.

Discoloration after full bloom: The flower becomes slightly darker as it ages.

Persistance: Two to three weeks.

Fragrance: Spicy.

Disease resistance: Resistant to fusarium and botrytis and virus tolerant as observed at Aurora, Oreg.

THE REPRODUCTIVE ORGANS

Stamens:

*Number.*—6.

*Arrangement.*—Typical of genus lilium.

*Anthers.*—Size: About 3.5 cm. Color: Red Purple 59-A.

*Filaments.*—Length: About 8 cm. Color: Yellow Green 145C-D.

*Pollen.*—Color: Orange 26-A.

Pistils:

*Number.*—1.

*Styles.*—Length: About 8.5 cm. Color: Yellow Green 144-A.

*Stigma.*—Color: Greyed Purple 186-A.

Character of ovaries: Typical of the genus lilium.

FRUIT

Fertility: The fruit is fertile.

Shape: Ovoid.

Color at maturity: Brown.

This new hybrid lily variety most nearly resembles the variety Star Gazer, U.S. Plant Pat. No. 4,085, but this new variety is taller than Star Gazer and has a darker rose color extending to the margins with the edges only being white.

I claim:

1. The new and distinct variety of Oriental Lily Hybrid, substantially as herein shown and described, characterized by its many flowers borne in raceme arrangement adjacent the upper end of a long, strong upright stem, the flowers being of a generally red purple coloration and the plant having abundant foliage and a vigorous, very strong growth habit.

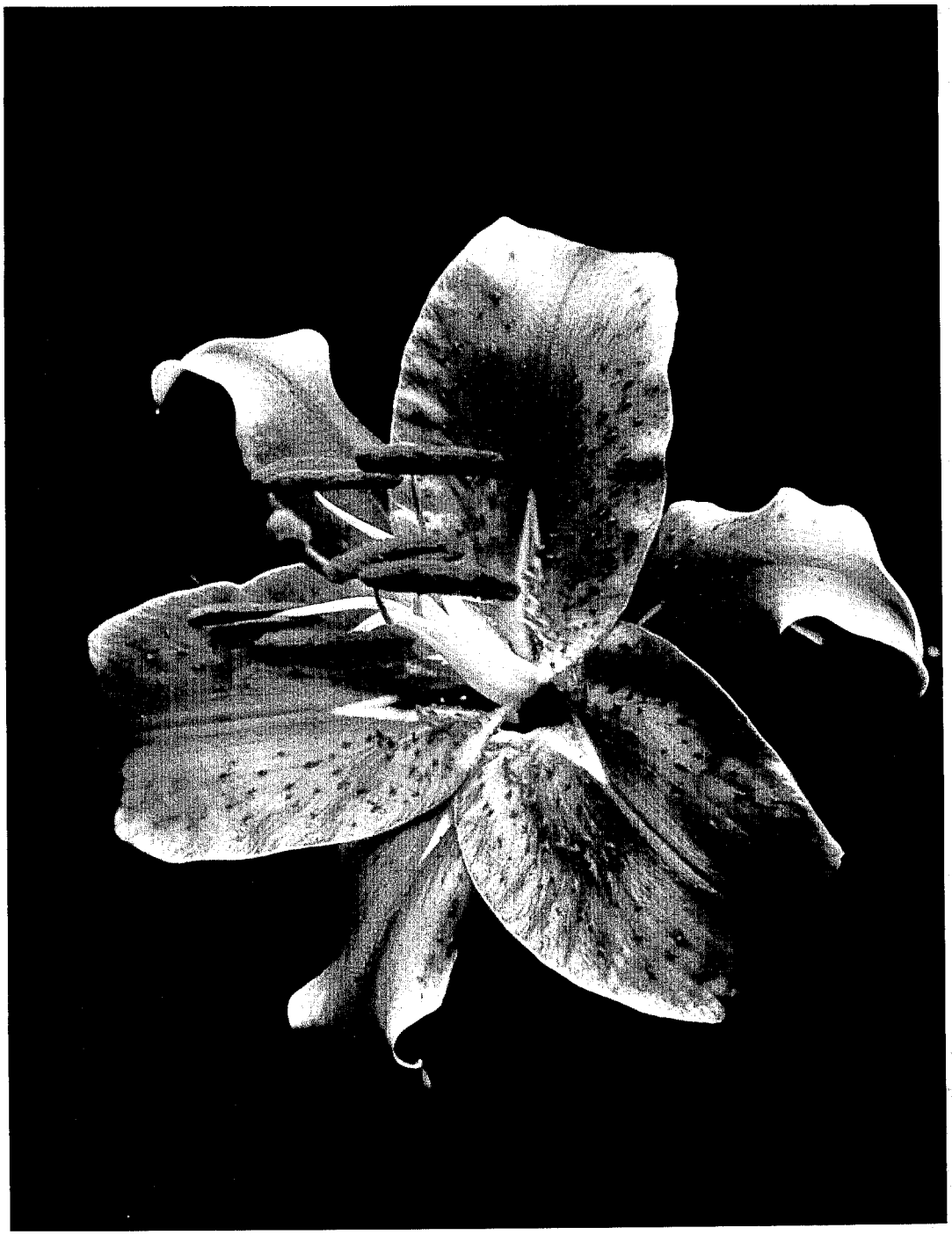

* * * * *